United States Patent [19]

Hashimoto et al.

[11] Patent Number: 5,112,863
[45] Date of Patent: May 12, 1992

[54] ANTIPSYCHOTIC DRUG

[75] Inventors: Atsushi Hashimoto, Tsukuba; Hidehiko Hibino, Tokyo; Osamu Nakachi, Ushiku, all of Japan

[73] Assignee: Nippon Oil & Fats Co., Ltd., Tokyo, Japan

[21] Appl. No.: 622,608

[22] Filed: Dec. 5, 1990

[30] Foreign Application Priority Data

Dec. 5, 1989 [JP] Japan ................ 1-314178
May 24, 1990 [JP] Japan ................ 2-132665

[51] Int. Cl.$^5$ .............................. A61K 31/24
[52] U.S. Cl. ................................. 514/534
[58] Field of Search .............. 514/534, 535, 561

[56] References Cited

PUBLICATIONS

Chem. Abst. 110-121477j (1989).

Primary Examiner—S. J. Friedman
Attorney, Agent, or Firm—Antonelli, Terry, Stout & Kraus

[57] ABSTRACT

The present invention provides an antipsychotic drug containing essentially an N-acyl amino acid derivative represented by the following general formula:

RCO-A wherein R indicates an alkyl or alkenyl having 1-25 carbon atoms, and A is an amino acid residue. The compound is similar to natural products and has little side effect by acting directly to brain cells after passing through easily the blood brain barrier.

7 Claims, No Drawings

ANTIPSYCHOTIC DRUG

BACKGROUND OF THE INVENTION

The present invention relates to an antipsychotic drug which comprises an N-acyl amino acid derivative as an active principle.

In 1951, H. Laborit found an antipsychotic action of chlorpromazine, and in 1952, J. Delay and P. Deniker introduced the compound into a medical treatment of schizophrenia. Then, they found clinical effectiveness, medical therapy of schizophrenia was started. Thereafter, antipsychotic drugs which comprise phenothiazine derivatives such as chlorpromazine and butyrophenone derivatives such as haloperidol have been developed.

In 1975, P. Seeman et al. and S. H. Snyder et al. found that that antipsychotic drugs could reveal the function by blocking dopamine receptor and by controlling dopamine activity. Further, in case of schizophrenia, since it was known that dopamine activity was excessively increased in the mesocortical system and the mesolimbic system, a dopamine hypothesis had appeared.

An antagonist of dopamine gives splendid effect to positive symptoms of acute schizophrenia, such as hallucination, delusion, thought disorder, excitation, etc.. On the other hand, no medicines for treating negative symptoms of chronic schizophrenia, such as feeling insensibility, desolation conditions, etc. are produced, so that the treatment of the chronic schizophrenia depends on an occupational therapy or life guidance under existing circumstances.

Epilepsy is a chronic disease repeating spastic fits. It has become apparent that antiepileptics act on a benzodiazepine receptor which conjugates with a $\gamma$-aminobutyric acid (GABA) receptor and increases the action of the GABA receptor to show antiepileptic functions.

On the other hand, schizophrenia is a disease principally showing acute positive symptoms such as hallucination, delusion, etc. and chronic negative symptoms such as feeling insensibility, lowering of volitions, etc.. In recent years, it has been considered that the schizophrenia is caused by depression of an N-methyl-D-asparatate (NMD-Asp) receptor which is a glutamic acid receptor (Clinical Neuropharmacology, 12(1), 1-13, 1989).

In Japanese Patent Publication No. 1-37373 and Japanese Patent Publication No. 63-9491, 2-pentanoyl amino acetic acid and 2-n-pentyl amino aceto amide having anticonvulsant functions for convulsion induced with bicuculline which is an antagonist specific for GABA were disclosed. It has become apparent that these compounds show the anticonvulsant functions via a GABA system (Biochemical Pharmacol., 32, 2751-2755, 1983).

However, these compounds are useful for epilepsy, and do not act on schizophrenia.

Since phencyclidine causes a person to have schizophrenia conditions of positive symptoms and negative symptoms, the study of intracelebral effects of phencyclidine is useful as means of systematically learning the beginning of both symptoms and finding the medicines for treating the negative symptoms. Lately, concerning an in-vitro test in elecrophysiological and biochemical study, phencyclidine has an effect on a specific binding site in an ion channel which conjugates with an excitatory amino acid receptor of an N-methyl-D-asparaginic acid type. As a result, it is found that nervous conduction via the N-methyl-D-asparaginic acid receptor is inhibited without a rival. On the other hand, since the N-methyl-D-asparaginic acid receptor has a strychnineinsensitive glycine binding site (an allosteric site), effective agents such as glycine, D-serine, D-alanine, etc. are differed from medicines such as phencyclidine and the like. These agents are known as a material promoting the action of N-methyl-D-asparaginic acid receptor.

Antipsychotic drugs such as said chlorpromazine give unsatisfactorily side effect, for example, myogelosis, mouth dry, sleepiness and constipation. In addition, even if the above amino acids such as glycine and the like are dosed in a living body, these can not pass through blood brain barrier and can not well act as an activator of the N-methyl-D-asparaginic acid receptor.

SUMMARY OF THE INVENTION

An object of the present invention is to provide a new antipsychotic drug containing essentially a compound which is similar to natural products and has little side effect by acting directly to brain cells after passing through easily the blood brain barrier.

The inventors of the present invention carried out research for resolving the above problems and obtaining a new compound. They found that N-acyl amino acid represented by the following general formula has an antipsychotic action to experimental animals.

Namely, the present invention provides an antipsychotic drug containing essentially N-acyl amino acid derivative represented by the general formula:

RCO-A wherein R indicates an alkyl or alkenyl group having 1-25 carbon atoms, and A is an amino acid residue.

In the above general formula, RCO- shows a fatty acid residue, specifically, butyryl, pentanoyl, hexanoyl, octanoyl, nonanoyl, lauroyl, myristoyl, palmitoyl, stearoyl, oleoyl, linoleoyl, arachidonoyl, eicosapentaenoyl, docosahexaenoyl, etc. are exemplificative. These groups are saturated or unsaturated fatty acid groups having even-numbered carbon chains. These saturated or unsaturated fatty acids found in a living body become the source of energy by decomposing at a normal lipid metabolic system, and they are preferred fatty acids because they have no toxic effect. Furthermore, saturated or unsaturated fatty acids having uneven-numbered carbon chains or branched chains may be used.

R is alkyl or alkenyl of 1-25 carbon atoms. When the carbon number is 0, the compound shows strong hydrophilic nature, and they can not pass through blood brain barriers. When the carbon number is 26 or more, the molecular weight of the compound becomes big and a large quantity of dosage should be given. As a result, the compound produces side effect.

Moreover, A indicates a natural or synthetic amino acid residue in said general formula. Particularly, glycine, D-serine, D-alanine, L-serine, L-alanine, D-cycloserine, D-cysteine, D-homoserine, O-phospho-D-serine are preferably used as $\alpha$-amino acids. Glycine, D-serine and D-alanine can be used more preferably. Accordingly, the compounds of the present invention contain all compounds which are constituted by the combination of the above groups, and the following compounds can be exemplificative.

N-butyrylglycine
N-butyryl-D-serine

N-butyryl-D-alanine
N-isobutyrylglycine
N-isobutyryl-D-serine
N-isobutyryl-D-alanine
N-pentanoylglycine
N-pentanoyl-D-serine
N-pentanoyl-D-alanine
N-hexanoylglycine
N-hexanoyl-D-serine
N-hexanoyl-D-alanine
N-2-ethylhexanoylglycine
N-2-ethylhexanoyl-D-serine
N-2-ethylhexanoyl-D-alanine
N-myristoylglycine
N-myristoyl-D-serine
N-myristoyl-D-alanine
N-oleoylglycine
N-oleoyl-D-serine
N-oleoyl-D-alanine
N-linolenoylglicine
N-linolenoyl-D-serine
N-linolenoyl-D-alanine
N-eicosapentaenoylglycine
N-eicosapentaenoyl-D-serine
N-eicosapentaenoyl-D-alanine
N-docosahexanoylglycine
N-docosahexanoyl-D-serine
N-docosahexanoyl-D-alanine Moreover, the salts of these compounds can be used in the present invention. In general, salts of sodium, potassium, calcium or the like can be used.

The compounds represented by said general formula can be synthesized by reacting a natural fatty acid and a natural amino acid in the presence of a catalyst such as 4-hydroxyphenyldimethylsulfomethyl sulfate, dicyclohexylcarbodiimide or the like.

The antipsychotic drug of the present invention containing essentially the compounds represented by said general formula can be dosed orally or non-orally. Namely, the agents can be orally dosed in the form of tablets, capsules, syrup, suspension, etc.. Otherwise, the agents can be non-orally dosed in the form of solution, emulsion, suspension, etc. by using injection and the like. For preparing these agents, common vehicles, disintegrators binders, lubricants, dyes, diluents and the like can be added.

The dose and dosage times are determined by the condition of illness, age, weight, dosage form, etc., and the agents can be dosed by 1–10,000 mg, preferably 10–5,000 mg per adult.

The merits of the present invention are as follows.

The antipsychotic drugs of the present invention exhibit remarkable antipsychotic action after passing through blood brain barriers by dosing to a living body. Further, N-acyl amino acid derivatives essentially contained in the drugs have little toxicity, and they are safe and useful as an agent for the prevention and medical treatment of schizophrenia, because the compounds consist of fatty acids and amino acids which are found in the natural world.

DESCRIPTION OF PREFERRED EMBODIMENTS

The following examples illustrate the present invention more specifically.

EXAMPLE 1

D-serine 2.0 g (0.02 mol) and triethylamine 2.8 ml (0.02 mol) were dissolved in 60 ml of water. Myristate of 4-hydroxyphenyldimethylsulfomethyl sulfate (trade name: SANCELER My-DSP, manufactured by Sanshin Kagaku Kogyo Co., Ltd.) 9.52 g (0.02 mol) was added to the solution, and the mixture was stirred for 12 hours at room temperature. The solution reacted was adjusted to pH 2 or 3 with 1N-HCl and the mixture was extracted with ethyl acetate. The ethyl acetate layer was dried over anhydrous sodium sulfate, and freed of solvent in vacuo. The oily residue obtained was purified by column chromatography (column: 2.5 × 15 cm) on 50 g of silica gel and N-myristoyl-D-serine 3.8 g was obtained.

EXAMPLE 2

D-alanine 1.78 g (0.02 mol) and triethylamine 2.8 ml (0.02 mol) were dissolved in 60 ml of water. Myristate of 4-hydroxyphenyldimethylsulfomethyl sulfate 9.52 g (0.02 mol) was added to the solution, and the mixture was stirred for 12 hours at room temperature. The solution reacted was adjusted to pH 2 or 3 with 1N-HCl and the mixture was extracted with ethyl acetate. The ethyl acetate layer was dried over anhydrous sodium sulfate, and freed of solvent in vacuo. The oily residue obtained was purified by column chromatography (column: 2.5 × 15 cm) on 50 g of silica gel and N-myristoyl-D-alanine 3.6 g was obtained.

EXAMPLE 3

4-hydroxyphenyldimethylsulfomethyl sulfate (trade name: SANCELER-DSP, manufactured by Sanshin Kagaku Kogyo Co., Ltd.) 2.66 g (0.01 mol) was heated and dissolved in 40 ml of acetonitrile. Docosahexaenoic acid 3.28 g (0.01 mol) was added to the solution obtained in a stream of nitrogen, and stirred at 0° C. To the mixture solution, dicyclohexyl carbodiimide 2.06 g (0.01 mol) was added little by little, and the solution was stirred for 2 hours at 0° C. and then for 2 hours at room temperature. The solution reacted was filtered to remove dicyclohexyl urea, and the filtrate was distilled in vacuo to obtain oily residue. D-serine 1.05 g (0.01 mol) and triethyl amine 1.4 ml (0.01 mol) were added to 10 ml of water. An acetonitrile solution of the above oily residue was added to the mixture with stirring, and stirred for 10 hours at room temperature. After reaction, the reaction mixture was concentrated under reduced pressure. The concentrate was adjusted to pH 2 or 3 with 6N-HCl, and extracted with ethyl acetate. The ethyl acetate layer was washed with water, dried over anhydrous sodium acetate, and freed of solvent in vacuo. The oily residue obtained was purified by column chromatography (column: 2.5 × 15 cm) on 50 g of silica gel and N-docosahexaenoyl-D-serine 1.7 g was obtained.

EXAMPLE 4

4-hydroxyphenyldimethylsulfomethyl sulfate 2.66 g (0.01 mol) was heated and dissolved in 40 ml of acetonitrile. Docosahexaenoic acid 3.28 g (0.01 mol) was added to the solution obtained in a stream of nitrogen, and the mixture was stirred at 0° C. To the mixture solution, dicyclohexyl carbodiimide 2.06 g (0.01 mol) was added little by little, and the solution was stirred for 2 hours at 0° C. and then for 2 hours at room temperature. The solution reacted was filtered to remove dicyclohexyl urea, and the filtrate was distilled in vacuo to obtain oily residue. D-alanine 0.89 g (0.01 mol) and triethyl amine 1.4 ml (0.01 mol) were added to 10 ml of water. An acetonitrile solution of the above oily residue was added to the mixture with stirring, and stirred for 10 hours at room temperature. After reaction, the reaction mixture was concentrated under reduced pressure. The concentrate was adjusted to pH 2 or 3 with 6N-HCl, and extracted with ethyl acetate. The ethyl acetate layer was washed with water, dried over anhydrous sodium acetate, and freed of solvent in vacuo. The oily residue obtained was purified by column chromatography (column: 2.5×15 cm) on 50 g of silica gel and N-docosahexaenoyl-D-alanine 1.6 g was obtained.

EXAMPLE 5

4-hydroxyphenyldimethylsulfomethyl sulfate 2.66 g (0.01 mol) was heated and dissolved in 40 ml of acetonitrile. Oleic acid 2.82 g (0.01 mol) was added to the solution obtained, and the mixture was stirred at 0° C. To the mixture solution, dicyclohexyl carbodiimide 2.06 g (0.01 mol) was added little by little, and the solution was stirred for 2 hours at 0° C. and then for 2 hours at room temperature. The solution reacted was filtered to remove dicyclohexyl urea, and the filtrate was distilled in vacuo to obtain oily residue. D-serine 1.05 g (0.01 mol) and triethyl amine 1.4 ml (0.01 mol) were added to 10 ml of water. An acetonitrile solution of the above oily residue was added to the mixture with stirring, and stirred for 10 hours at room temperature. After reaction, the reaction mixture was concentrated under reduced pressure. The concentrate was adjusted to pH 2 or 3 with 6N-HCl, and extracted with ethyl acetate. The ethyl acetate layer was washed with water, dried over anhydrous sodium acetate, and freed of solvent in vacuo. The oily residue obtained was purified by column chromatography (column: 2.5×15 cm) on 50 g of silica gel and N-oleoyl-D-serine 1.5 g was obtained.

EXAMPLE 6

D-serine 2.0 g (0.02 mole) and triethylamine 2.8 ml (0.02 mol) were dissolved in 60 ml of water. Myristate of 4-hydroxyphenyldimethylsufomethyl sulfate (trade name: SANCELER My-DSP, manufactured by Sanshin Kagaku Kogyo Co. Ltd.) 9.52 g (0.02 mol) was added to the solution, and the mixture was stirred for 12 hours at room temperature. The solution reacted was adjusted to pH 2 or 3 with 1N-HCl and the mixture was extracted with ethyl acetate. The ethyl acetate layer was dried over anhydrous sodium sulfate, and freed of solvent in vacuo. The residue obtained was dissolved in ethyl acetate - methanol (3:1), and the solution was adjusted to pH 11 with a 10% solution of sodium hydroxide. After observation of precipitates, the solution was concentrated under reduced pressure. The product crystallized was washed with ethyl acetate and then hexane to obtain 3.1 g of N-myristoyl-D-serine sodium salt.

EXAMPLE 7

4-hydroxyphenyldimethylsufomethyl sulfate (trade name: SANCELER-DSP, manufactured by Sanshin Kagaku Kogyo Co. Ltd.) 2.66 g (0.01 mole) was heated and dissolved in 40 ml of acetonitrile. Pentanoic acid 1.16 g (0.01 mol) was added to the solution obtained, and the mixture was stirred at 0° C. To the mixture solution, dicyclohexyl carbodiimide 2.06 g (0.01 mol) was added little by little, and the solution was stirred for 2 hours at 0° C. and then for 2 hours at room temperature. The solution reacted was filtered to remove dicyclohexyl urea, and the filtrate was distilled in vacuo to obtain oily residue. D-serine 1.05 g (0.01 mol) and triethyl amine 1.4 ml (0.01 mol) were added to 10 ml of water. An acetonitrile solution of the above oily residue was added to the mixture with stirring, and stirred for 10 hours at room temperature. After reaction, the reaction mixture was concentrated under reduced pressure. The concentrate was adjusted to pH 2 or 3 with 6N-HCl, and extracted with ethyl acetate. The ethyl acetate layer was washed with water, dried over anhydrous sodium acetate, and freed of solvent in vacuo. The oily residue obtained was purified by column chromatography (column: 2.5×15 cm) on 50 g of silica gel and N-pentanoyl-D-serine 1.7 g was obtained.

Preparation were made by using N-acyl amino acid derivatives obtained in these examples as an active component.

Preparation Example 1 (Tablet)
The following ingredients are contained in a tablet (150 mg).

| | | |
|---|---|---|
| Active component | | 50 mg |
| Lactose | | 48 mg |
| Starch | | 50 mg |
| Polyvinyl pyrrolidone | | 1.5 mg |
| Magnesium stearate | | 0.5 mg |
| | Total | 150 mg |

Preparation Example 2 (Capsule)
The following ingredients are contained in a gelatin

| | | |
|---|---|---|
| Active component | | 50 mg |
| Lactose | | 59.5 mg |
| Starch | | 40 mg |
| Soft silicic anhydride | | 0.5 mg |
| | Total | 150 mg |

Preparation Example 3 (Granule)
The following ingredients are contained in 1 g of granules.

| | | |
|---|---|---|
| Active component | | 200 mg |
| Lactose | | 450 mg |
| Starch | | 300 mg |
| Hydroxypropyl cellulose | | 50 mg |
| | Total | 1000 mg |

Toxicity test
Compounds of the present invention obtained in Examples 1-7 were suspended in 0.1% Tween 80 solution, respectively. Each solution was dosed in the abdomen of Wistar rats having 180 g to 200 g of body-weight. As a result, $LD_{50}$ was 700 mg/kg or more.

Antipsychotic action test
Method: the action of antipsychotic was estimated by a method of Sturgen et al. (Eur. J. Pharmacol 76, 37–53, 1981). Namely, medicines suspended in 0.1% Tween 80 were dosed in the abdomen of Wistar rats (Weight: 200–250 g, 6 rats/group). After ten minutes, phencyclidine dissolved in physiological saline (10 mg/kg) was dosed intraperitoneally. After ten minutes, locomotor activity and stereotypy score were estimated at intervals of 20 minutes by 6 grades.

Rats were anesthetized with pentobarbital (40 mg/kg, intruperitoneally) and mounted on a stereotaxic frame.

For the intracranical administration of 7-chlorokynurenicocid, the guide cannulae were fixed to the skull. Beginning 5-7 days after surgery, bilateral intracranial injections were performed in the non-anesthetized rats with cannulae attached by poly ethylene tubes to two 10 μl Hamilton syringes. The injection site was A.P. −0.8 (anterior to bregma), V. +2.0, L.±1.5 according to the atlas of Paxinos and Watson (1982). The medicine 5 μl was injected in four minutes a minute after inserting the needle. After the injection the injection needle was kept in the brain for five minutes and removed. After ten minutes from the beginning of the injection, phencyclidine was dosed intraperitoneally. After ten minutes, the change of action was observed at intervals of 20 minutes.

A. Locomotor activity
 0. As usual.
 1. Sometimes, movement within localized area of cage.
 2. Movement over a small area of cage, intermittent activity emitted at a low-moderate rate.
 3. Movement over a small area of cage, activity emitted continuously and at a moderate-rapid rate.
 4. Movement over a large area of cage, activety is intermittent and emitted at a low-moderate rate.
 5. Movement over a large area of cage, activety is emitted continuously and at a moderate-rapid rate.

B. Stereotypy score
 0. As usual.
 1. Locomotor activity, sniffing and grooming more frequent than observed for control.
 2. Higher frequency of sniffing, rearing or turning than in 1.
 3. Moderate rate and intermittent sniffing, rearing, turning or backpedaling.
 4. Rapid rate and continuous turning, backpedaling, sniffing.
 5. Dyokinetic extension and flexion of limbs, head and neck. Result: In the locomotor activity (Tables 1 and 3) and the stereotypy score (Tables 2 and 4) observed 30 minutes after pretreatment with N-myristoyl-D-serine (NMD-Ser) and N-myristoyl-D-alanine (NMD-Ala) and dosage of phencyclidine, the scores lessen with the decrease of the dose. In the group dosed more than 50 mg/kg of medicines, statistical significant difference ($P < 0.01$) is found. In the group dosed 100 mg/kg of medicines, the locomotor activity and the stereotypy score are nearly controlled. Moreover, in the dosage of N-pentanoyl-D-serine, N-docosahexaenoyl-D-serine, N-docosahexaenoyl-D-alanine and N-oleoyl-D-serine, the same effect is observed.

Further, when N-myristoyl-D-serine 200 mg/kg and 7-chlorokynurenic acid which is an allosteric antagonist of a glycine binding site are dosed in the brain, the locomotor activity and the stereotypy score observed at a dose of N-myristoyl-D-serine alone are not observed. As a result, it is proved that N-acyl amino acids derivatives act in cells of the brain.

TABLE 1

| NMD-Ser* (mg/kg) | Locomotor activity Score |
|---|---|
| 0 | 3.6 ± 0.2 |
| 1 | 3.7 ± 0.2 |
| 10 | 3.3 ± 0.2 |
| 50 | 2.0 ± 0.3** |
| 100 | 1.5 ± 0.5** |

TABLE 1-continued

| NMD-Ser* (mg/kg) | Locomotor activity Score |
|---|---|
| 200 | 1.5 ± 0.3** |

*N-myristoyl-D-serine
**$P < 0.01$

TABLE 2

| NMD-Ser* (mg/kg) | Stereotypy score Score |
|---|---|
| 0 | 3.3 ± 0.3 |
| 1 | 3.2 ± 0.3 |
| 10 | 3.2 ± 0.3 |
| 50 | 1.7 ± 0.2** |
| 100 | 1.2 ± 0.3** |
| 200 | 1.5 ± 0.2** |

*N-myristoyl-D-serine
**$P < 0.01$

TABLE 3

| NMD-Ala* (mg/kg) | Locomotor activity Score |
|---|---|
| 0 | 3.0 ± 0.4 |
| 1 | 2.8 ± 0.2 |
| 10 | 2.4 ± 0.4 |
| 50 | 2.2 ± 0.4** |
| 100 | 0.7 ± 0.3** |
| 200 | 1.5 ± 0.3** |

*N-myristoyl-D-alanine
**$P < 0.01$

TABLE 4

| NMD-Ala* (mg/kg) | Stereotypy score Score |
|---|---|
| 0 | 3.3 ± 0.5 |
| 1 | 3.0 ± 0.4 |
| 10 | 2.4 ± 0.2 |
| 50 | 2.0 ± 0.3** |
| 100 | 0.8 ± 0.3** |
| 200 | 1.3 ± 0.4** |

*N-myristoyl-D-alanine
**$P < 0.01$

We claim:

1. An antipsychotic drug for oral or intravenous administration which comprises an active amount of an N-acyl amino acid derivative represented by the following general formula:

RCO-A wherein R represents an alkyl or alkenyl group having 1-25 carbon atoms, and A is an amino acid residue and a pharmaceutically acceptable carrier or vehicle for said administration.

2. The antipsychotic drug as claimed in claim 1, wherein the RCO- shows a fatty acid residue selected from the group consisting of butyryl, pentanoyl, hexanoyl, octanoyl, nananoyl, lauroyl, myristoyl, palmitoyl, stearoyl, oleoyl, linoleoyl, arachidonoyl, eicosapentaenoyl and docosahexaenoyl.

3. The antipsychotic drug as claimed in claim 1, wherein the amino acid residue is selected from the group consisting of glycine, D-serine, D-alanine, L-serine, L-alanine, D-cycloserine, D-cysteine, D-homoserine and O-phospho-D-serine.

4. The antipsychotic drug as claimed in claim 3, wherein the amino acid residue is glycine, D-serine or D-alanine.

5. The antipsychotic drug as claimed in claim 1, wherein the N-acyl amino acid derivative is selected from the group consisting of N-butyrylglycine, N-butyryl-D-serine, N-butyryl-D-alanine, N-isobutyrylglycine, N-isobutyryl-D-serine, N-isobutyryl-D-alanine, N-pentanoyl-glycine, N-pentanoyl-D-serine, N-pentanoyl-D-alanine, N-hexanoylglycine, N-hexanoyl-D-serine, N-hexanoyl-D-alanine, N-2-ethylhexanoylglycine, N-2-ethylhexanoyl-D-serine, N-2-ethylhexanoyl-D-alanine, N-myristoylglycine, N-myristoyl-D-serine, N-myristoyl-D-alanine, N-oleoylglycine, N-oleoyl-D-serine, N-oleoyl-D-alanine, N-linolenoylglicine, N-linolenoyl-D-serine, N-linolenoyl-D-alanine, N-eicosapentaenoylglycine, N-eicosapentaenoyl-D-serine, N-eicosapentaenoyl-D-alanine, N-docosahexanoylglycine, N-docosahexanoyl-D-serine and N-docosahexanoyl-D-alanine, and the salts thereof.

6. The antipsychotic drug as claimed in claim 5, wherein the salt is a sodium salt, potassium salt or calcium salt.

7. The anti-psychotic drug as claimed in claim 1, wherein the N-acyl amino acid derivative is selected from the group consisting of N-myristoyl-D-serine, N-myristoyl-D-alanine, N-docosahexaenoyl-D-serine, N-docosahexaenoyl-D-alanine, N-oleoyl-D-serine and N-pentanoyl-D-serine.

* * * * *